(12) United States Patent
Meyer et al.

(10) Patent No.: US 6,959,591 B2
(45) Date of Patent: Nov. 1, 2005

(54) TEST STAND FOR INTERNAL COMBUSTION ENGINE

(75) Inventors: Philippe Meyer, Ronquerolles (FR); Frédéric Guimbal, Paris (FR); Daniel Chouard, Paris (FR)

(73) Assignee: Montupet S.A., (FR)

( * ) Notice: Subject to any disclaimer, the term of this patent is extended or adjusted under 35 U.S.C. 154(b) by 0 days.

(21) Appl. No.: 10/221,537

(22) PCT Filed: Mar. 9, 2001

(86) PCT No.: PCT/FR01/00721

§ 371 (c)(1),
(2), (4) Date: Feb. 26, 2003

(87) PCT Pub. No.: WO01/69195

PCT Pub. Date: Sep. 20, 2001

(65) Prior Publication Data

US 2003/0159499 A1    Aug. 28, 2003

(30) Foreign Application Priority Data

Mar. 10, 2000  (FR) .................................. 00 03075

(51) Int. Cl.[7] ............................................ G01M 15/00
(52) U.S. Cl. ..................................... 73/119 R; 73/49.7
(58) Field of Search .............................. 73/40, 46, 47, 73/49.7, 116, 117.2, 117.3, 118.1, 119 R

(56) References Cited

U.S. PATENT DOCUMENTS

| | | | | |
|---|---|---|---|---|
| 3,751,978 A | * | 8/1973 | Crawford | .................... 73/49.7 |
| 4,448,065 A | | 5/1984 | Meurer | |
| 5,054,314 A | * | 10/1991 | Cofflard et al. | ............ 73/118.1 |
| 5,272,911 A | * | 12/1993 | Beggs et al. | ................. 73/49.7 |
| 5,585,549 A | * | 12/1996 | Brevick et al. | .............. 73/49.7 |

FOREIGN PATENT DOCUMENTS

EP              0747687         12/1996

* cited by examiner

Primary Examiner—Eric S. McCall
(74) Attorney, Agent, or Firm—Blakely Sokoloff Taylor & Zafman

(57) ABSTRACT

A test stand for cylinder head components of an internal combustion engine includes at least one combustion or pressure chamber. The test stand supplies a hydraulic fluid to the chamber, and controls the pressure of the hydraulic fluid to simulate pressure cycles in the chamber. The test stand controls the pressure with at least one source of high-pressure hydraulic fluid, the high-pressure being at an adjustable and constant level, at least one solenoid valve per chamber, receiving hydraulic fluid from the high-pressure source, and automatically drives each solenoid valve as a function of the pressure in the chamber and a set-point pressure, so that each solenoid valve feeds this chamber with hydraulic fluid the pressure of which is controlled at any time by the solenoid valve and simulates predetermined pressure cycles as a function of time.

20 Claims, 4 Drawing Sheets

TEST STAND FOR INTERNAL COMBUSTION ENGINE

This is a non-provisional application claiming the benefit of International application number PCT FR01/00721 filed Mar. 9, 2001.

BACKGROUND OF THE INVENTION

1. Field of the Invention

The present invention relates to a test stand for a cylinder head of an internal combustion engine or for any part located in its immediate environment, such as a cylinder head gasket, fastening screw, etc., said engine comprising at least one combustion or pressure chamber. More particularly, it relates to such a stand for cylinder head components comprising at least means for supplying a hydraulic fluid to the combustion or pressure chamber, and means for controlling the pressure of this fluid so as to simulate pressure cycles in the combustion or pressure chamber.

These test stands are designed to accommodate either an engine cylinder head alone or a cylinder head mounted on its engine block. Pressurized hydraulic fluid is introduced into the combustion or pressure chambers, while a heat-transfer fluid is made to flow in the cooling pipes of the cylinder head with or without a block in order to keep it at a predetermined operating temperature. The means for controlling the pressure of the hydraulic fluid are designed to vary this pressure cyclically so as to simulate the operating cycles of the engine.

The operating conditions of the engine both with regard to the temperature in one or more water chambers and to the pressure in the combustion or pressure chamber are therefore reproduced by means of such a test stand. It is thus possible to study its behavior under thermal and mechanical stresses and its fatigue resistance, and consequently to optimize its design with regard to its layout and to the alloys used, the molding and machining methods or the heat treatments carried out.

Furthermore, such test stands may be used to study the behavior of some parts in the immediate environment of the cylinder head, such as the cylinder head gasket, fastening screws, etc.

2. Description of Related Art

A test stand of the type summarized above is known through document EP-A-0 415 857.

In that document, the means for controlling the pressure of the hydraulic fluid in the combustion or pressure chambers consist of injection pumps, the pistons of which are set in motion by cams rotated by an electric motor. The profile of a pressure cycle is therefore mainly determined by the shape of the cams.

In general, such a device is satisfactory. It is however relatively limited because the pressure cycles are produced in a purely mechanical manner.

In the first place, the duration of each cycle cannot be reduced as much as would be desirable in order to simulate engine speeds which are constantly tending to increase.

The design of current test stands also has limitations with regard to the maximum pressure to be reached. Now the maximum pressures in the combustion chambers are tending to increase for diesel engines.

Finally, the profile of the operating cycle is fixed by the shape of the cams. Therefore it cannot be adjusted with great accuracy, or easily modified.

Furthermore, maintenance of the stand is relatively expensive since it requires changing the camshaft, generally after several hundred hours of operation. This is because the cams wear rapidly with time, and their profile changes, thus impairing the regularity of the operating cycles.

The present invention aims to alleviate these drawbacks.

More specifically, the aim of the invention is to provide a stand for testing fatigue in cylinder heads alone or in cylinder heads mounted on an engine block, which makes it possible to reproduce more faithfully the pressure cycles on a cylinder head of an internal combustion engine at the operating temperature of the cooling circuit.

The aim of the invention is also to provide such a test stand which can reach higher operating frequencies and pressures.

The aim of the invention is also to provide such a test stand, the maintenance of which is easier and less expensive than that of existing test stands.

BRIEF SUMMARY OF THE INVENTION

To this end, the subject of the invention is a test stand for cylinder head components of an internal combustion engine comprising at least one combustion or pressure chamber, said test stand comprising at least means for supplying a hydraulic fluid to the combustion or pressure chamber, and means for controlling the pressure of this fluid so as to simulate pressure cycles in the combustion or pressure chamber, characterized in that said control means comprise at least one source of high-pressure hydraulic fluid, at least one solenoid valve per combustion or pressure chamber in order to supply this combustion or pressure chamber with hydraulic fluid from the high-pressure source, and control means in order to drive each solenoid valve as a function of the pressure in the combustion or pressure chamber and a set-point pressure.

First of all, it will be observed that the term "cylinder head components" refers here, especially in the claims, not only to the cylinder head itself, but also to all the parts appearing in its immediate environment. The test stand according to the invention may in fact be used equally well to test such parts as it may be used to test the cylinder head itself.

Moreover, the term "solenoid valve" refers to any device, also called a servovalve, making it possible to connect, and more particularly to put in communication, in a controlled manner, a source of pressurized fluid placed upstream of the device with a user circuit located downstream, so as to control the pressure in this user circuit. Such a solenoid valve generally has two chambers and a slide valve controlled so as to put one of the chambers in relation, depending on its position, with a high-pressure supply circuit and the other chamber with a low-pressure fluid return circuit, one of the chambers furthermore being connected to the user circuit.

It will be noted that included in the devices of this type are pulsators, in which the pressure source is not put directly in communication with the user circuit, but is operationally connected to it via a vibrating piston, itself controlled by a solenoid valve.

In the test stand according to the invention, the pressure of the hydraulic fluid in the combustion or pressure chambers is therefore controlled by solenoid valves supplied from a high-pressure fluid source. It is therefore no longer necessary to provide an injection pump rotating at high speed in order to simulate high engine speeds. Only the solenoid valves have to have a high dynamic range.

Moreover, it is easier to reach the high pressures which are currently required.

Furthermore, the profile of a pressure cycle can be set arbitrarily by changing the set-point pressure, and modified without any mechanical intervention by simply modifying the program running the test stand.

Finally, the cams of the prior art are omitted, which has the result not only of reducing the maintenance costs of the stand, but also of providing better reproducibility of the operating cycle.

In a particular embodiment, the test stand according to the invention comprises a hydraulic block in which channels are made, forming at least part of the means of supplying hydraulic fluid to the combustion or pressure chamber and means for returning the hydraulic fluid to the hydraulic fluid source, said solenoid valve being mounted on said hydraulic block.

Also in a particular embodiment of the invention, the test stand comprises means for creating a first calibrated leak in each combustion or pressure chamber, said leak being designed to shape the signal detected by said pressure sensor.

More particularly, said means for creating a first calibrated leak in each combustion or pressure chamber may comprise a flow restriction between the combustion or pressure chamber and a circuit for returning hydraulic fluid.

This leak, located at the high point of the circuit, also provides a function of purging the waste air.

Even more particularly, said flow restriction between the combustion or pressure chamber and the hydraulic fluid return circuit may be mounted at the location of a spark plug or of the fuel injector in the cylinder head.

Also in a particular embodiment of the invention, means are provided for creating a second calibrated leak in each combustion or pressure chamber, said leak being designed to adjust the pressure gradient in the combustion or pressure chamber during the decompression phases of the pressure cycles.

More particularly, said means for creating a second calibrated leak in each combustion or pressure chamber comprise a calibrated pipe between a chamber of the solenoid valve and a hydraulic fluid return circuit.

Even more particularly, said calibrated pipe may be formed in said hydraulic block.

Also in a particular embodiment of the invention, the test stand comprises a circuit for flushing the hydraulic fluid from each combustion or pressure chamber.

This flushing circuit makes it possible to purge the circuits and the combustion or pressure chambers at chosen time intervals, so as to take the impurities contained in the hydraulic fluid to the return circuit. These impurities, coming from deterioration of the cylinder head and/or the cylinder head gasket, are then filtered before recycling the hydraulic fluid to the high-pressure source.

The flushing circuit of the hydraulic fluid may especially comprise means for creating a vacuum in the combustion or pressure chamber so as to adjust the pressure gradient in the decompression phase.

More particularly, the means for creating a vacuum may comprise a flushing pipe between the combustion or pressure chamber and a hydraulic fluid return circuit.

This flushing circuit may be formed in said hydraulic block.

In a particular embodiment, the flushing circuit comprises a fluid channel between one chamber of the solenoid valve and a hydraulic fluid return circuit, a flushing solenoid valve, and a connection forming an ejector between said flushing pipe and said fluid channel.

More particularly, a control pipe may be provided in order to control said flushing solenoid valve from means of supplying hydraulic fluid to the combustion or pressure chamber.

Also according to one embodiment of the invention, the test stand comprises leak detection means.

It is thus possible, from a certain leak level characterizing the start of failure, to follow the change in these leaks until the actual failure occurs.

This device will consist, for example, in periodically pressurizing at least one of the circuits and in then isolating and controlling the change in pressure over time.

Also in a particular embodiment, the stand according to the invention comprises at least one pressure sensor for measuring the pressure in each combustion or pressure chamber.

The subject of the invention is also a hydraulic block for a test stand as described above, characterized in that it comprises holes for supplying hydraulic fluid to the combustion or pressure chamber of a cylinder head capable of being mounted on the block, from a source of high-pressure hydraulic fluid capable of being connected to said block, holes for return of fluid from the combustion or pressure chamber to the hydraulic fluid source, and means of assembling and connecting at least one solenoid valve for controlling the flow of hydraulic fluid between the fluid supply holes and the fluid return holes.

In a particular embodiment, the hydraulic block according to the invention further comprises calibrated leak holes between the control solenoid valve and the fluid return holes.

Also in a particular embodiment, the hydraulic block according to the invention further comprises flushing holes between the combustion or pressure chamber and the fluid return holes.

More particularly, provision may be made in the hydraulic block for means for mounting at least one flushing solenoid valve for controlling the flow of fluid in the flushing holes Even more particularly, the hydraulic block according to the invention may comprise holes for controlling the flushing solenoid valve from fluid supply holes.

The subject of the invention is also a method of testing at least a cylinder head component of an internal combustion engine comprising at least one combustion or pressure chamber, said method comprising at least the steps consisting in supplying a hydraulic fluid to the combustion or pressure chamber, and in controlling the pressure of this fluid so as to simulate pressure cycles in the combustion or pressure chamber, characterized in that it further comprises the steps consisting in establishing a program for changing a set-point pressure in the combustion or pressure chambers;

in measuring the pressure in each combustion or pressure chamber; and in operating at least one solenoid valve per combustion or pressure chamber, designed to control the pressure of the hydraulic fluid in the combustion or pressure chamber, so as to automatically control the pressure measured at the set-point pressure.

In a particular embodiment, the method according to the invention comprises at least one step of flushing the hydraulic fluid from the combustion or pressure chamber.

The method according to the invention may furthermore comprise a crack detection step.

BRIEF DESCRIPTION OF THE DRAWINGS

A particular embodiment of the invention will now be described, by way of nonlimiting example, with set-point to the appended schematic drawings in which.

DETAILED DESCRIPTION OF THE INVENTION

Figure 1:
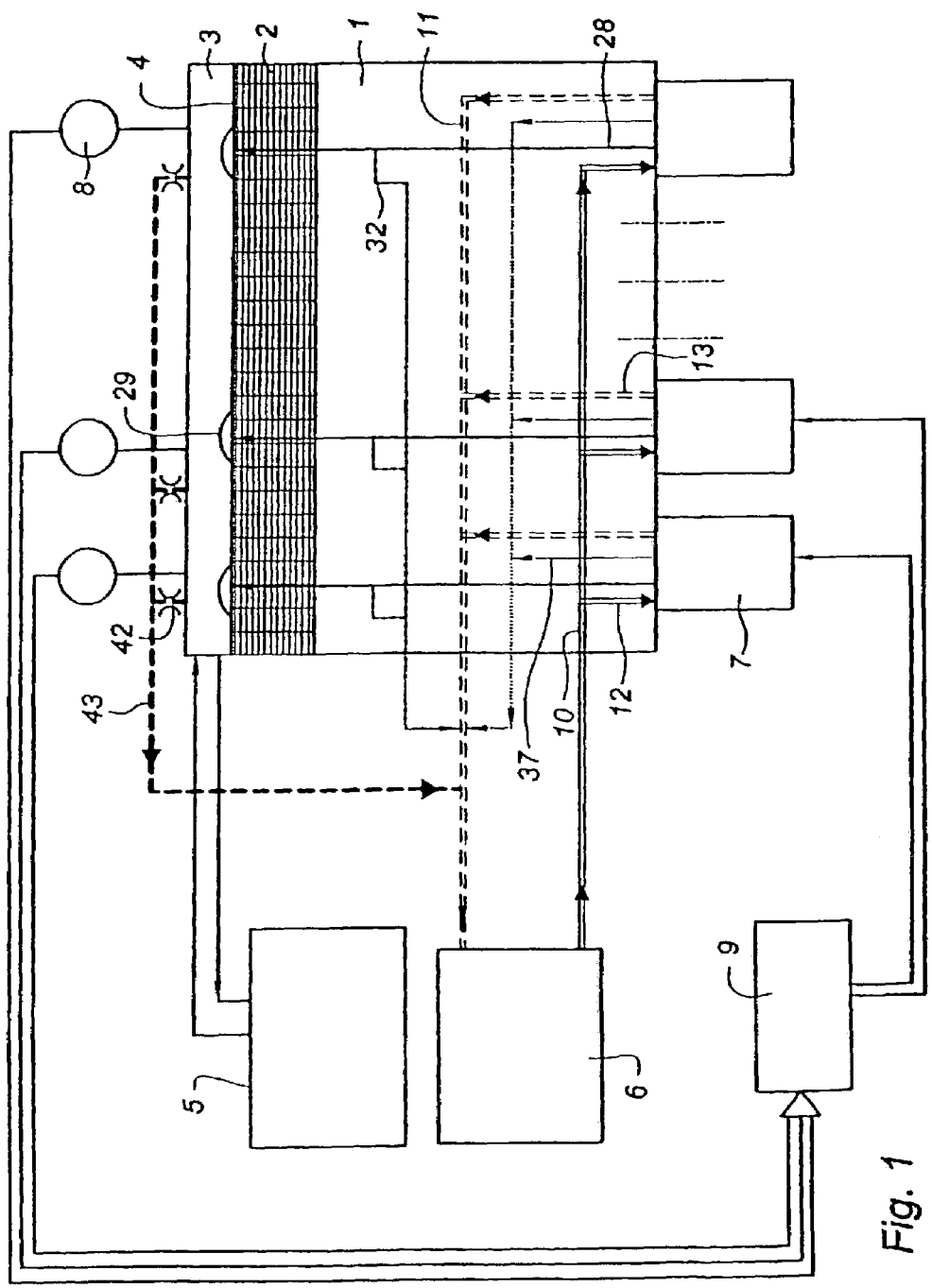
FIG. 1 is an outline diagram of a test stand according to the present invention.

FIG. 1 shows a cylinder head fatigue test stand comprising, in a known manner, a hydraulic block 1 and an interface 2. The cylinder head 3 may be directly mounted on the interface 2 with insertion of a cylinder head gasket (not shown) or with its engine block.

The interface 2 is in the form of a parallelepipedal plate, the upper face 4 of which is machined to the layout of the cylinder head studied with regard especially to the distance between axes of the cylinders, the water intake, the housings for the fastening screws and the chamber volume at the top dead center. The other faces of the interface 2 are adapted to the layout of the basic hydraulic block 1 and to the distribution of the heat-transfer fluid.

It will be observed that the cylinder head, with or without its engine block, is mounted on the interface 2, preferably with its ostandinal screws. This is because the whole device must reproduce as faithfully as possible the clamping stresses in the cylinder head as they exist in a cylinder head mounted on an engine block.

FIG. 1 further shows two hydraulic units 5 and 6, one 5 for a heat-transfer fluid, and the other 6 for the pressurized hydraulic fluid. The two fluids are identical with regard to their composition so that mixing them does not interfere with operation of the stand when leaks occur prior to failure of the cylinder head during testing.

The temperature control is well known per se in the prior art and will therefore not be further described in detail.

A certain number of solenoid valves 7 for controlling pressure are mounted on the hydraulic block 1, and pressure sensors 8 are mounted on the cylinder head or at any suitable point in the hydraulic circuit. The sensors 8 are connected to a control and detection unit 9 which controls the solenoid valves 7. The solenoid valves 7 are mounted on the block 1 by any suitable means such as screws (not shown).

The control and detection unit 9 also makes it possible to detect leaks in the cylinder head from information supplied by the sensors 8, and thus to detect failure initiators. The unit 9 and the sensors 8 therefore form a crack detection system.

Figure 3:
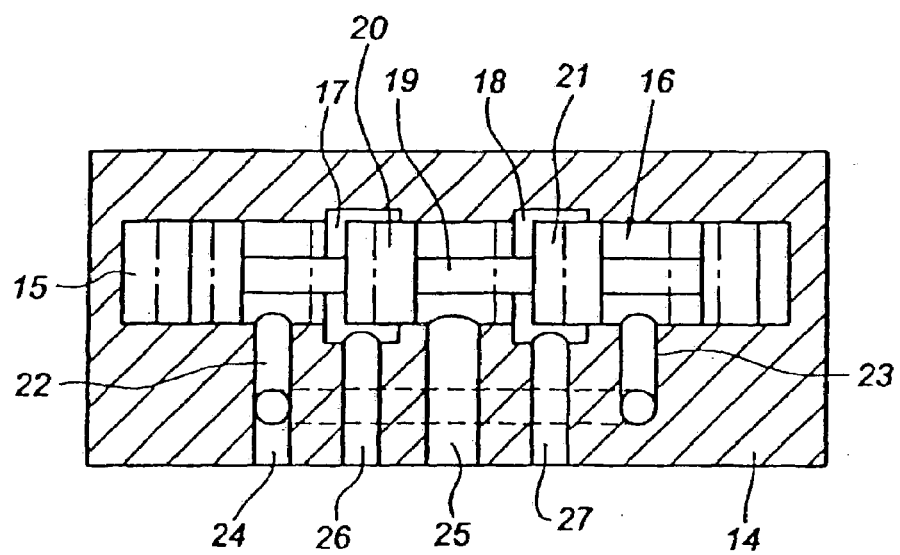
FIG. 3 shows in longitudinal section a solenoid valve capable of being used in the invention.
Figure 4:
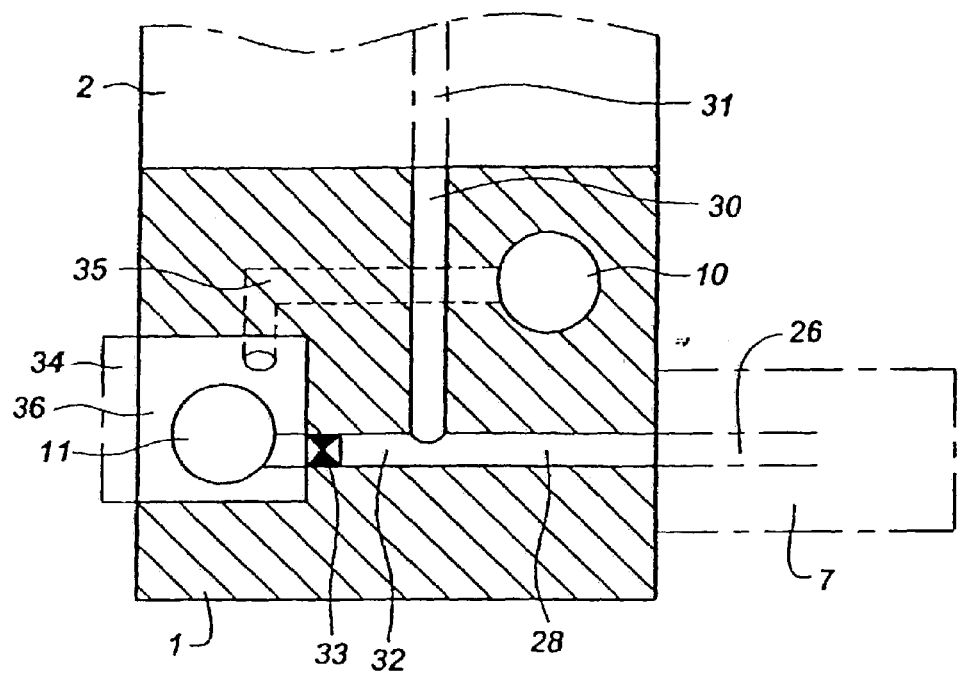
FIG. 4 is another side view in section of the hydraulic block of the test stand, illustrating the flushing means.
Figure 5:
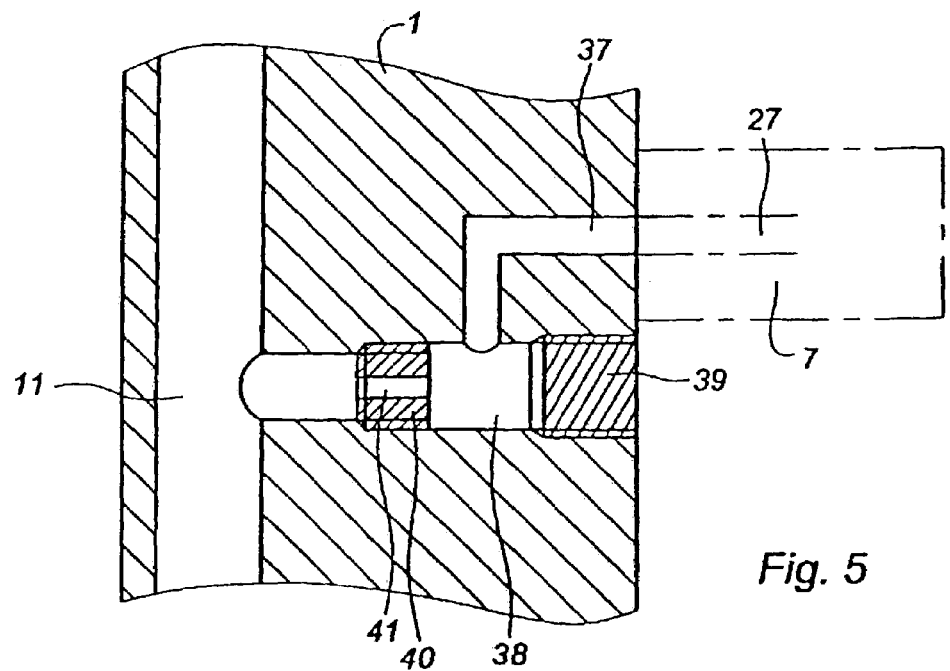
FIG. 5 is a top view in section illustrating the controlled leak means.

The hydraulic block 1 and the interface 2 in this case comprise six identical "sections" such that it is possible to adapt cylinder heads of engines having up to six cylinders to them. FIGS. 3 to 5 correspond to one of these sections.

This test stand may however accommodate cylinder heads of engines with less than six cylinders provided the orifices of the unused sections are closed. Of course, test stands according to the invention could be produced for cylinder heads of an engine with more than six cylinders, by increasing the corresponding number of sections.

Figure 2:
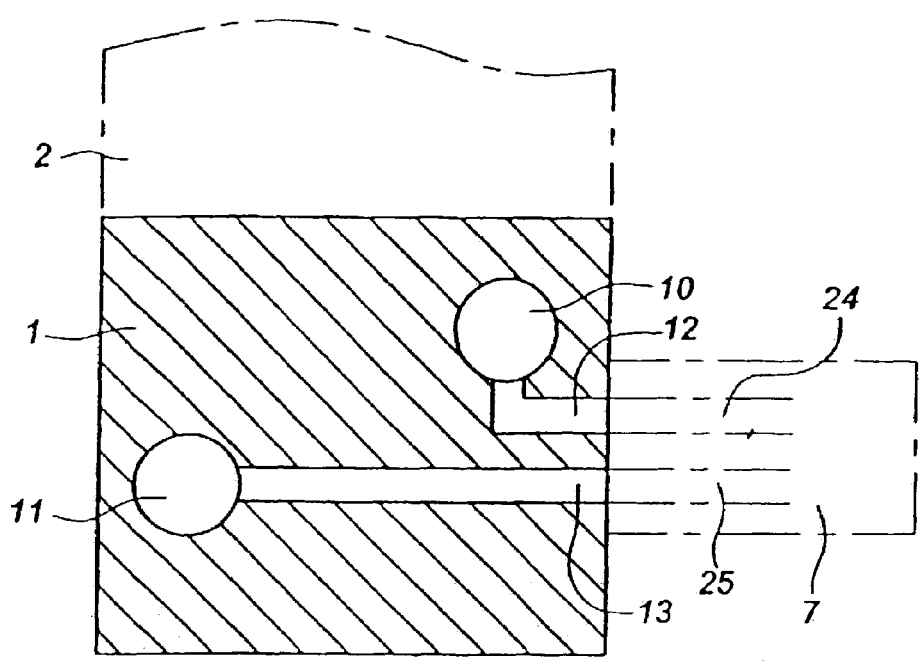
FIG. 2 is a side view in section of the hydraulic block of this test stand.

As shown in particular in FIG. 2, the hydraulic block 1 first of all comprises two fluid supply 10 and fluid return 11 longitudinal holes, which pass through all the sections of the block.

The hole 10 is connected to the output of the hydraulic unit 6 in order to feed the solenoid valves 7 with high-pressure hydraulic fluid. To this end, the hole 10 is also connected to the inlets of the solenoid valves 7 via a set of distribution pipes 12.

The hole 11 is connected to the tank of the hydraulic unit 6 so that the hydraulic fluid can return to this unit, especially from the solenoid valves 7. To this end, the outlets of the solenoid valves 7 are connected to the hole 11 by a set of collecting pipes 13.

FIG. 3 shows in more detail a solenoid valve 7 of known type, capable of being mounted on the hydraulic block 1 for controlling the flow of fluid pressurized by the hydraulic unit 6.

This solenoid valve 7 comprises a body 14 in which a bore 15 is formed, accommodating a distribution slide valve 16 which can be moved axially. The bore 15 comprises two larger-diameter regions forming axially spaced chambers 17 and 18.

The distribution slide valve 16 mainly consists of a rod 19 and of two pistons 20 and 21 coaxial with this rod. The pistons 20 and 21 are spaced axially by the same distance as the regions 17 and 18 of the bore 15.

Five lateral pipes open out into the bore 15 in order to make it communicate with the outside.

Two lateral pipes 22 and 23 form two branches of the same pipe 24 for supplying pressurized hydraulic fluid. These two pipes 22 and 23 open out axially into the bore outside the chambers 17 and 18. The pipe 24 of each solenoid valve is connected to one of the distribution pipes 12.

The lateral pipe 25 opens out into the bore between the chambers 17 and 18. Its other end is connected to one of the collecting pipes 13.

The last two lateral pipes 26 and 27 each open out into one of the chambers 17 and 18, respectively. Their connection to the hydraulic block 1 will be seen below.

The distribution slide valve 16 is displaced by any suitable means (not shown), by means of an electrical connection to the control unit 9. It is possible, for example, to use the plunger of a suitably powered electromagnet, or an eccentric mounted at the free end of the shaft of a torque engine. These means are well known and will not be described in more detail.

When the distribution slide valve 16 is taken to its position shown by solid lines in FIG. 3, it is noticed that the pipe 26 is put in communication with the high pressure via the chamber 17 and the pipe 22, while the pipe 27 is put in communication with the fluid return via the chamber 18 and the pipe 25. Conversely, when the distribution slide valve 16 is taken to its position shown in dot-dashed lines in FIG. 3, the pipe 26 is put in communication with the fluid return via the chamber 18 and the pipe 25, while the pipe 27 is put in communication with the high pressure via the chamber 17 and the pipe 23.

If set-point is now made to FIG. 4, it can be seen that in each section of the hydraulic block 1, there is a pipe 28 for supplying hydraulic fluid to the respective combustion or pressure chamber 29 (FIG. 1) of the cylinder head 3, connected to the pipe 26 of the solenoid valve 7. The chamber is supplied from the pipe 28 via a branch pipe 30 in the block 1 and a connection pipe 31 formed in the interface 2.

The end 32 of the supply pipe 28, above its junction with the branch pipe 30, forms a flushing pipe which opens out into the fluid return hole 11 via a closure valve 33. The valve 33 is controlled by means of a flushing solenoid valve 34 actuated by high-pressure fluid brought from the hole 10 via a control pipe 35. To this end, the solenoid valve 34 is placed in a housing 36 made straddling the hole 11, so that it can be connected to the pipe 35 while at the same time allowing the flow of fluid in the hole 11.

Set-point will now be made to FIG. 5.

Each section of the hydraulic block 1 comprises a leak pipe 37 connected to the pipe 27 of the solenoid valve 7. The pipe 37 opens out into a hole 38 opening in its turn into the hole 11 for return of the hydraulic fluid. A plug 39 is screwed to the free-air end of the hole 38 to provide a sealed closure.

A member 40 having a calibrated orifice 41 is placed in the hole 38 between the connection to the pipe 37 and the connection to the hole 11.

When a solenoid valve 7 is in its configuration shown in solid lines in FIG. 3, the high pressure is transmitted to the corresponding combustion chamber 29 via pipes 24, 26 and 28. In contrast, when this solenoid valve 7 is in its configuration shown in dot-dashed lines in FIG. 3, the combustion or pressure chamber 29 is brought to the return pressure via pipes 25, 26 and 18.

It will be understood that each combustion or pressure chamber 29 is alternately subjected to the high pressure transmitted through the hole 10 and to the low pressure of the hole 11, with the alternating displacement of the distribution slide valve 16 in the bore 15. These displacements are controlled, according to a preestablished run program, by the control unit 9 which also synchronizes the various solenoid valves 7 in order to simulate engine cycles.

At chosen intervals, for example of about one hour, the solenoid valve 34 opens the valve 33, setting the pipe 28 to the return pressure of the hole 11. Next, fluid is sucked into the pipe 28, causing rapid flow toward the hole 11, which in turn leads to an effect of ejecting the fluid from the combustion chamber via the pipes 30 and 31.

In addition, it will be observed in FIG. 1 that flow restrictions 42 are formed on the leak lines 43 of the combustion or pressure chambers 29 toward the low pressure. These leak lines are in this case connected to the combustion or pressure chambers at the location of the injectors, and they make it possible to adjust the waveform of the signals picked up by the sensors 8.

Figure 6:
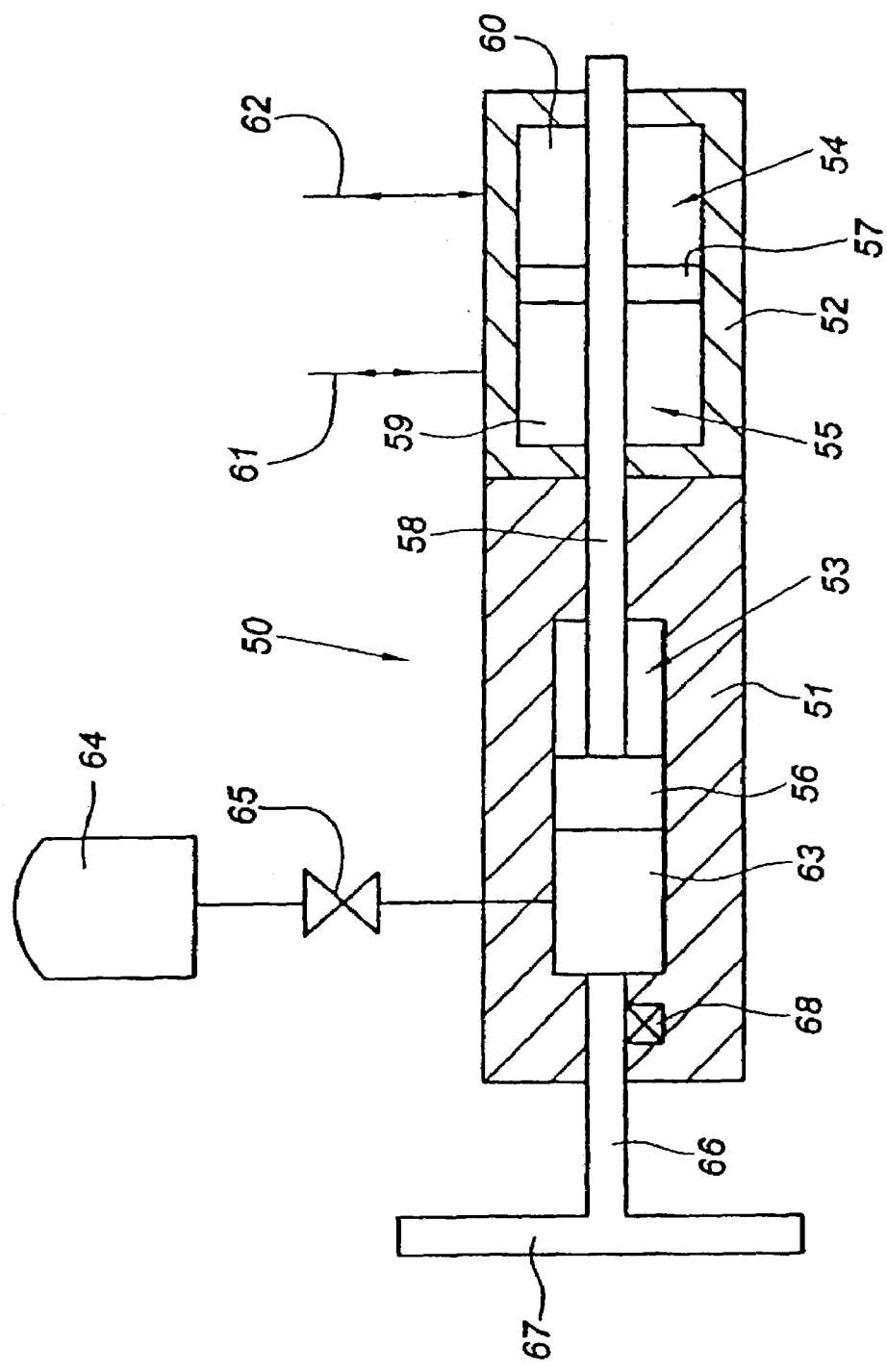
FIG. 6 is a side view in section illustrating the principle of a pulsator capable of being used in the invention.

The pulsator shown in FIG. 6 comprises, in general, a body 50 in two parts 51 and 52, each one delimiting a cylindrical housing 53 and 54, respectively.

A movable assembly 55 consists of a piston 56 moving in the housing 53, a piston 57 moving in the housing 54, the pistons 56 and 57 being connected by a rod 58.

The piston 57 divides the housing 54 into two chambers 59 and 60. Each of the chambers 59 and 60 is connected by a line 61 and 62, respectively, to one of the chambers of a solenoid valve (not shown).

The piston 56 delimits, in the housing 53, on the side away from the rod 58, a chamber 63 connected to a reservoir 64 of hydraulic fluid via a valve 65. Moreover, the chamber 63 is connected via a pipe 66 to another pipe 67 connected either in line or branched to the pressure chambers of the cylinder head being tested.

The pressure sensor 68 allows the aforementioned solenoid valve to be driven. The pressure in the chambers of the cylinder head is thus controlled by this solenoid valve, but via the pulsator.

We claim:

1. A test stand for cylinder head components of an internal combustion engine comprising at least one combustion or pressure chamber, said test stand comprising means for supplying a hydraulic fluid to the combustion or pressure chamber, and means for controlling the pressure of this fluid so as to simulate pressure cycles in the combustion or pressure chamber, wherein said means for controlling comprises:

at least one source of high-pressure hydraulic fluid, the high-pressure being monitored at a constant level which is adjustable, at least one solenoid valve per combustion or pressure chamber, receiving hydraulic fluid from the high-pressure source, and driving means in order to automatically drive each solenoid valve as a function of the pressure in the combustion or pressure chamber and predetermined pressure-time curve, so that each solenoid valve feeds the combustion or pressure chamber with hydraulic fluid the pressure of which is controlled at any time by the solenoid valve and simulates predetermined pressure cycles as a function of time, wherein said test stand comprises:

a hydraulic block in which channels are made, forming at least part of the means for supplying hydraulic fluid from the source of high-pressure hydraulic fluid to the solenoid valve and means for returning the hydraulic fluid from the solenoid valve to the hydraulic source which are continuously available, and means for creating a first calibrated leak in the hydraulic block for each combustion or pressure chamber, between the corresponding solenoid valve and the circuit for returning hydraulic fluid, said leak being designed to limit the flow of fluid in the return circuit when the corresponding chamber is not connected to the source of high pressure and to allow a quick reaction of the solenoid valve to make it able to regulate the pressure around the predetermined pressure-time curve.

2. The test stand as claimed in claim 1, comprising, in each combustion or pressure chamber, a pressure sensor for detecting the pressure in the chamber and means for creating a second calibrated leak said leak being arranged to shape the signal detected by said pressure sensor.

3. The test stand as claimed in claim 2, in which said means for creating the second calibrated leak in each combustion or pressure chamber comprise a flow restriction between the combustion or pressure chamber and a circuit for returning hydraulic fluid.

4. The test stand as claimed in claim 3, wherein the cylinder head is designed for receiving a spark plug or a fuel injector and said flow restriction between the combustion or pressure chamber and the hydraulic fluid return circuit is mounted at the location of the spark plug or of the fuel injector.

5. The test stand as claimed in claim 1, in which said means for creating a first calibrated leak in each combustion or pressure chamber comprise a calibrated pipe between a chamber of the solenoid valve and a hydraulic fluid return circuit.

6. The test stand as claimed in claim 5, comprising a circuit for flushing the hydraulic fluid from each combustion or pressure chamber.

7. The test stand as claimed in claim 6, in which the circuit for flushing hydraulic fluid comprises means for creating a vacuum in the combustion or pressure chamber.

8. The test stand as claimed in claim 7, in which the means for creating a vacuum comprise a flushing pipe between the combustion or pressure chamber and a hydraulic fluid return circuit.

9. The test stand as claimed in claim 1 or claim 8, in which said flushing pipe is formed in said hydraulic block.

10. The test stand as claimed in claim 8, comprising a fluid channel between one chamber of the solenoid valve and a hydraulic fluid return circuit, a flushing solenoid valve, and a connection forming an ejector between said flushing pipe and said fluid channel.

11. The test stand as claimed in claim 10, comprising a pipe for controlling said flushing solenoid valve from means of supplying hydraulic fluid to the combustion or pressure chamber.

12. The test stand as claimed in claim 11, comprising leak detection means.

13. The test stand as claimed in claim 12, comprising at least one pressure sensor (8) for measuring the pressure in each combustion or pressure chamber.

14. A hydraulic block for a test stand as claimed in claim 13, wherein it comprises holes for supplying hydraulic fluid to the combustion or pressure chamber of a cylinder head capable of being mounted on the block, from a source of high-pressure hydraulic fluid capable of being connected to said block, holes for return of fluid from the combustion or pressure chamber to the hydraulic fluid source, and means of assembling and connecting at least one solenoid valve for controlling the flow of hydraulic fluid between the fluid supply holes and the fluid return holes.

15. The hydraulic block as claimed in claim 14, comprising calibrated leak holes between the control solenoid valve and the fluid return holes.

16. The hydraulic block as claimed in claim 14 or claim 15, comprising flushing holes between the combustion or pressure chamber and the fluid return holes.

17. The hydraulic block as claimed in claim 16, comprising means for mounting at least one flushing solenoid valve for controlling the flow of fluid in the flushing holes.

18. The hydraulic block as claimed in claim 17, comprising holes for controlling the flushing solenoid valve from fluid supply holes.

19. A test stand as claimed in claim 1, in which the solenoid valves and their driving means are located out of the hydraulic block.

20. The test stand as claimed in claim 9, comprising a fluid channel between one chamber of the solenoid valve and a hydraulic fluid return circuit, a flushing solenoid valve, and a connection forming an ejector between said flushing pipe and said fluid channel.

* * * * *